US006993985B2

(12) United States Patent
Srebro

(10) Patent No.: US 6,993,985 B2
(45) Date of Patent: Feb. 7, 2006

(54) METHOD AND DEVICE FOR FLUID SAMPLING

(75) Inventor: David Edward Srebro, Brookfield, IL (US)

(73) Assignee: Toxair LLC, Orland Park, IL (US)

( * ) Notice: Subject to any disclaimer, the term of this patent is extended or adjusted under 35 U.S.C. 154(b) by 0 days.

(21) Appl. No.: 10/707,203

(22) Filed: Nov. 26, 2003

(65) Prior Publication Data

US 2004/0173034 A1 Sep. 9, 2004

Related U.S. Application Data

(60) Provisional application No. 60/451,809, filed on Mar. 4, 2003.

(51) Int. Cl.
*G01N 1/24* (2006.01)
*G01F 15/06* (2006.01)

(52) U.S. Cl. ............................. 73/864.34; 73/863.22; 73/863.23; 73/198

(58) Field of Classification Search ................................
73/863.22–863.25, 864.34, 864.35, 863.02, 73/863.03, 198–199
See application file for complete search history.

(56) References Cited

U.S. PATENT DOCUMENTS

| 4,478,025 A | 10/1984 | Scanlan ........................ 53/512 |
| 4,779,398 A | 10/1988 | Glandon et al. ............... 53/434 |
| 5,437,202 A | 8/1995 | Clark, II .................... 73/864.35 |
| 6,125,710 A * | 10/2000 | Sharp .................... 73/864.34 X |
| 6,325,978 B1 * | 12/2001 | Labuda et al. ................. 422/84 |
| 6,338,282 B1 | 1/2002 | Gilbert ..................... 73/864.34 |
| 6,571,954 B2 | 6/2003 | Nadler ....................... 206/522 |
| 6,815,211 B1 * | 11/2004 | Blazewicz et al. .......... 436/166 |
| 2004/0055363 A1 * | 3/2004 | Bristol ...................... 73/198 X |

FOREIGN PATENT DOCUMENTS

DE 2351570 A * 4/1975

* cited by examiner

*Primary Examiner*—Thomas P. Noland

(57) ABSTRACT

A fluid stream sampler enables variable flow rate controlled air sampling, as an attachment to a vacuum source, typically a household vacuum cleaner. The fluid stream sampler includes a housing body having a vacuum outlet opening and a sampling port inlet. A volumetric flow rate indicator is disposed in the flowpath between the vacuum outlet opening and the sampling port inlet. An adjustable damper panel interposed in the flowpath regulates the vacuum pressure within the housing body. In operation, a vacuum imparted by the vacuum source directs a fluid stream along the flowpath between the vacuum outlet opening and the sampling port inlet such that, upon moving the damper panel to a desired position within the flowpath, a desired volumetric flow rate is achieved as measured by the indicator. The desired volumetric flow rate corresponds to a preferred flow rate specified for a fluid constituent sampling medium interposed in the flowpath at the sampling port inlet. A fluid stream sampler enables gas bag sampling, as an attachment to a vacuum chamber, typically a paper shipping tube. The vacuum chamber includes a vacuum outlet opening and an inlet. A gas bag is disposed in the chamber. A self-sealing valve is disposed in the bag and a straw is disposed in the valve. The straw having an inlet exterior to the vacuum chamber and an outlet interior to the gas bag. Whereby a vacuum imparted by the fluid stream sampler at the outlet port directs a pressure drop interior to the vacuum chamber and a pressure differential effect on the gas bag, such that, a fluid stream is developed through the straw and collected in the gas bag.

9 Claims, 5 Drawing Sheets

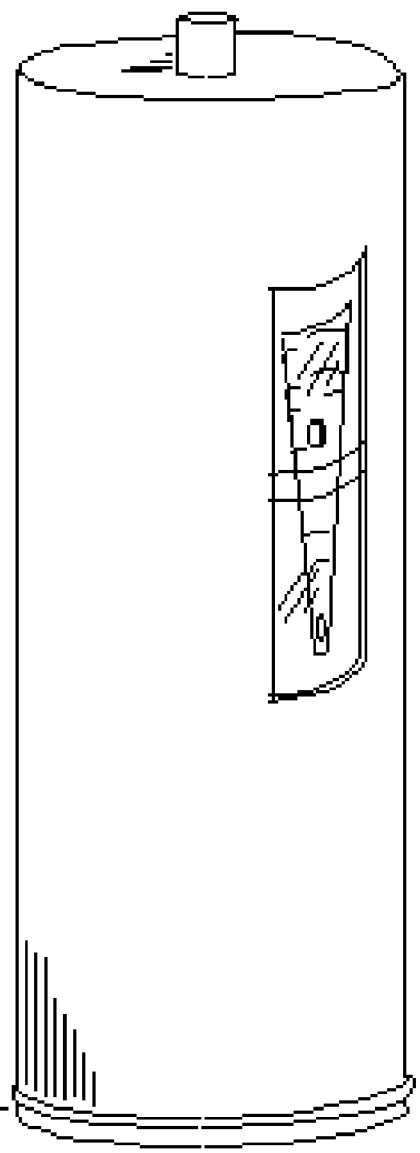
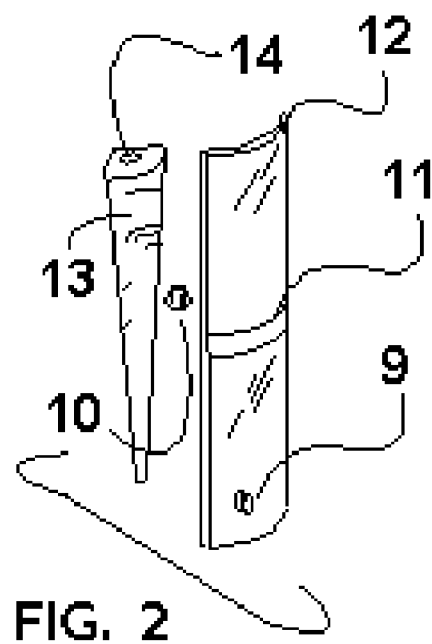
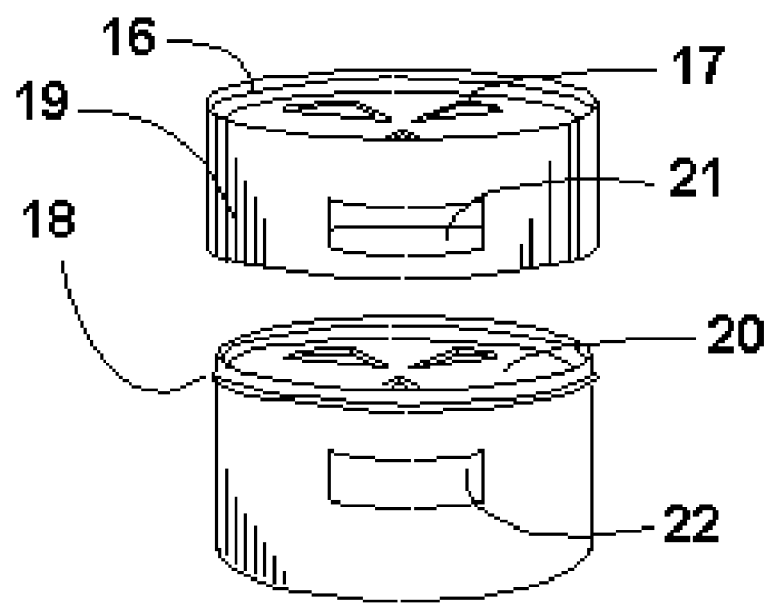

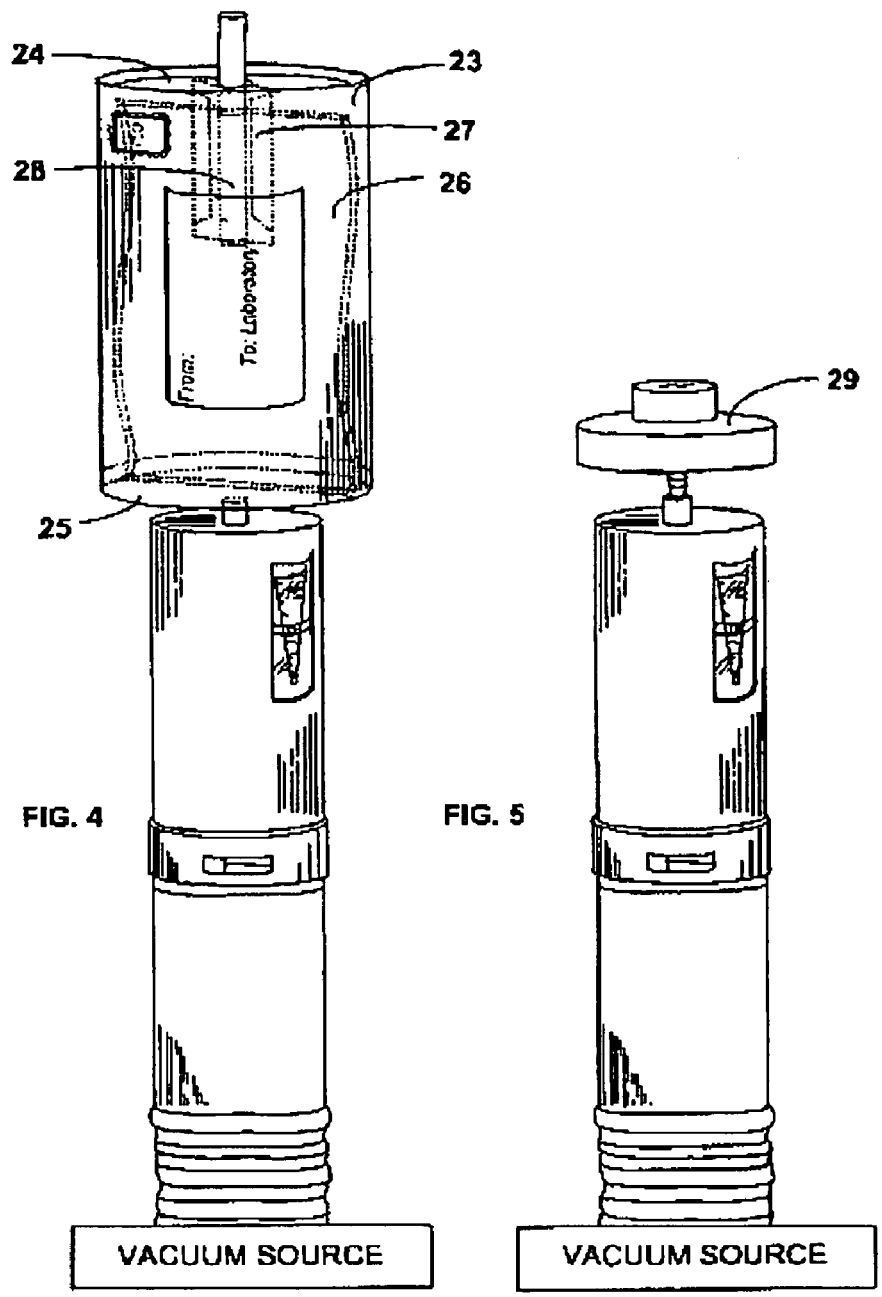

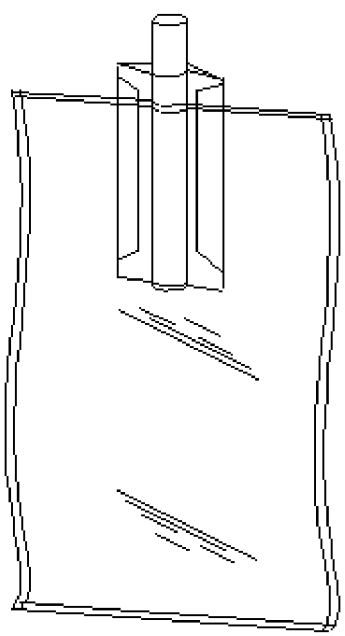
FIG. 12
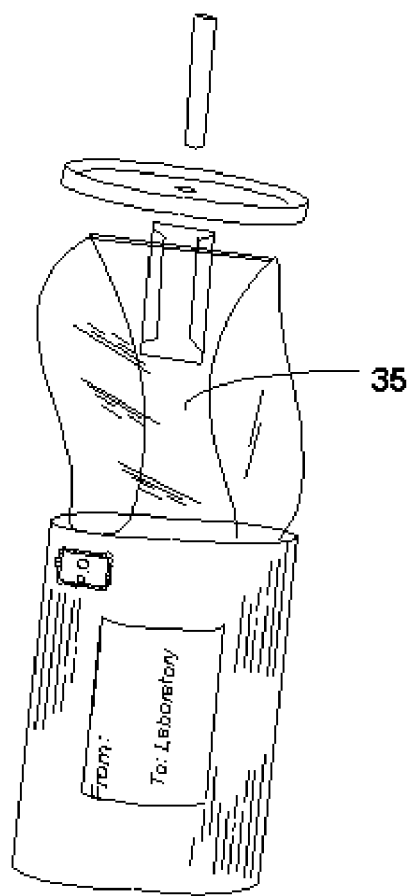
FIG. 14
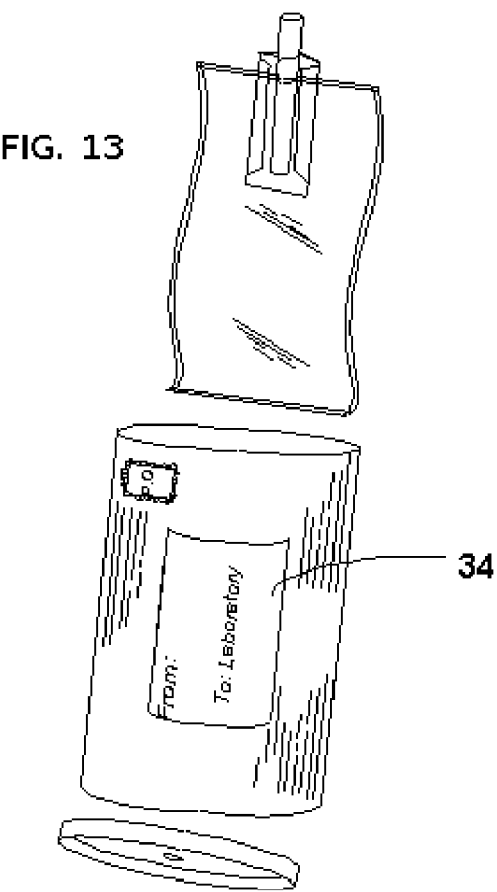
FIG. 13

METHOD AND DEVICE FOR FLUID SAMPLING

CROSS REFERENCE TO RELATED APPLICATIONS

This application claims the benefit of U.S. Provisional Application No. 60/451,809 filed on Mar. 4, 2003.

BACKGROUND OF INVENTION

1. Field of the Invention

The present invention generally relates to a method and device for fluid sampling, and more particularly, to a fluid stream sampler that permits the detection and measurement of constituents of a fluid stream that is directed through the sampler and a method to capture and transport a sample of the fluid stream for subsequent analytical laboratory analysis.

2. Background of the Invention

In conventional fluid stream sampling the collection of samples for aerosol analysis of fluid (typically air) stream constituents, employing either slit impaction cassette media, micro porous filter media or inflatable gas bag media technology, was typically accomplished by fixing the media in line to a vacuum pump sized for the specific sampling event. The vacuum pump would have a air stream flow indicator and air stream flow metering regulator set in line with the air stream which could then be metered to vary the flow rate for calibration or in another variation of the prior art the pump motor speed was electrically adjusted to vary the flow rate for calibration specification and then the rate was verified by a stand alone electronic flow indicator meter, of which many varieties exist. Conventional sample media technology demands that flow rates are known so total volume sampled can be calculated to develop representative analytical data for the overall environment being tested. Additionally, sample media technology requires that optimal particulate trace dispersion on split impaction cassette media or micro porous filter media will occur if the air flow rate is regulated based on the media manufacturer's recommendations and in gas bag media technology air flow rate is regulated so as to fill the bag at a controlled rate to prevent accidental bag rupture from rapid over inflation. The conventional approach to collecting fluid stream samples is not conducive to those persons who are not highly skilled and experienced in fluid stream sampling. The operation of conventional fluid sampling devices requires, for example, prior knowledge of vacuum pump generation technology to properly size the pump to be employed as the vacuum source, as well as to properly select the properly sized air flow gauge or electronic calibrator. The operation of conventional fluid sampling devices also requires specialized knowledge as to how such devices are properly read and interpreted so as to ensure that a properly regulated flow rate is obtained from the vacuum source, as well as specialized knowledge as to how such rates optimize the particular mode of media being employed. The operation of conventional fluid sampling devices when applied to a conventional vacuum chamber to obtain a gas bag media sample also requires specialized knowledge as to how the fluid stream is properly directed to aspirate the gas bag media by differential pressure at a regulated rate according to standard operating procedures promulgated by governmental environmental regulatory bodies. Lastly, conventional fluid sampling methods often require a constituent sample media that has been employed for sampling to be returned to the laboratory for subsequent analysis. Often times the laboratory is at a great distance from the sampled source and postal shipping is required with the media being packaged as a additional event to the sampling event in distinct and independent elements, typically cardboard boxes.

The present fluid (typically air) stream sampler device with flow rate controller and indicator provides a improved variable flow rate-controlled air sampler that overcomes the shortcomings of conventional devices that employ distinct and independent elements to achieve a measurable volumetric flow rate. In accordance with the present device, the mass flow indicator in the form of a element, commonly known as a rotameter, is an element that is integral to the device, and consists of a vertical flow tube structure molded directly into the sides of the sampler shell body. Additionally, a variable damper panel is held in position by annular friction fit protrusions molded into the side of the sampler shell body to firmly stabilize the damper when moved under negative pressure flows.

The present fluid stream sampler provides an improved variable flow rate controlled air sampler in which the flow rate can be set over a wide range by a fine axial adjustment of the damper panel, flow rates being limited only by the strength of the vacuum source (conveniently a household vacuum cleaner) and calibrated by the visual indicator of a ball floating between calibration lines drawn on the window to the rotameter.

The present fluid stream sampler also provides an improved variable flow rate controlled air sampler that can be operated by persons who do not necessarily have the specialized skills and experience of persons who operate conventional devices of this type.

The present fluid stream sampler also provides an improved variable flow rate controlled air sampler in which the primary components can be concurrently formed in a injection molded process during manufacture of a thermoplastic embodiment of the fluid stream sampler.

The present fluid stream sampler also provides an improved method to obtain a fluid sample by improving a vacuum chamber gas bag fill component of the sampler which overcomes the shortcomings of conventional gas bag vacuum chamber fill component with the gas bag subcomponent requiring a rigid fill port valve element and a distinct and independent shipping container element. In accordance with the present device, the fill port valve of the gas bag subcomponent is an element that is integral to the bag, and consists of a two-ply flexible film structure which self-seals upon removal of the fill port straw. Additionally, the vacuum chamber component (conveniently a paper shipping tube) for the present fluid stream sampler serves a secondary and integral function as the protective shipping container of the gas bag which contains the fluid sample.

SUMMARY OF INVENTION

Objects of the Invention

The present fluid stream sampler enables variable flow rate controlled air sampling, as an attachment to a vacuum source, typically a conventional household vacuum cleaner. The fluid stream sampler includes a housing body having a vacuum outlet opening formed therein, a sampling port inlet formed therein, and a flowpath extending between the outlet and the inlet. A volumetric flow rate indicator is disposed in the flowpath between the vacuum outlet opening and the sampling port inlet. A hose, fluidly connected at one end to a vacuum source, has a fitting at the other end that is insertable into the vacuum outlet opening. An adjustable damper panel interposed in the flowpath regulates the vacuum pressure within the housing body. In operation, a vacuum imparted by the vacuum source directs a fluid stream through the housing body along the flowpath between the vacuum outlet opening and the sampling port inlet such that, upon moving the damper panel to a desired within the flowpath, a desired volumetric flow rate is achieve as measured by the indicator, the desired volumetric flow rate corresponding to a preferred flow rate specified for a fluid constituent sampling medium interposed in the flowpath at the sampling port inlet.

In a preferred embodiment, the vacuum source is a conventional household vacuum cleaner. The preferred volumetric flow rate indicator is a rotameter. The preferred fluid constituent sampling medium are either a split impaction sampling cassette, a micro porous filter sampling cassette or a vacuum chamber gas bag. The preferred vacuum chamber component is a conventional paper shipping tube. The preferred gas bag subassembly subcomponent is a two-ply plastic film gas bag with a integral two-ply plastic film self-sealing fill port valve. The most preferred media is capable of collecting at least one of particulate and gaseous air for subsequent biological and chemical analysis.

BRIEF DESCRIPTION OF DRAWINGS

FIG. 2 illustrates the fluid stream sampler of FIG. 1 as an exploded perspective view showing the volumetric flow rate indicator as being a rotameter.

FIG. 3 illustrates the fluid stream sampler of FIG. 1, as an exploded perspective view showing the movable damper panel.

FIG. 4 illustrates the fluid stream sampler of FIG. 1, showing the sampling media (here a vacuum chamber) disposed in the sampling port inlet and the hose inserted into the vacuum outlet opening. Gas Bag subassembly is internal to the vacuum chamber and is represented by a dashed outline.

FIG. 5 illustrates the fluid stream sampler of FIG. 1, showing the sampling media (here a split impaction cassette) disposed in the sampling port inlet and the hose inserted into the vacuum outlet opening.

FIG. 12 is a elevation view of the gas bag subassembly.

FIG. 13 is a exploded perspective view of the vacuum chamber of FIG. 4 illustrating the gas bag prior to sampling.

FIG. 14 is a exploded perspective view of the vacuum chamber of FIG. 4 illustrating the gas bag after collection of a gaseous air sample.

DETAILED DESCRIPTION

Figure 1:
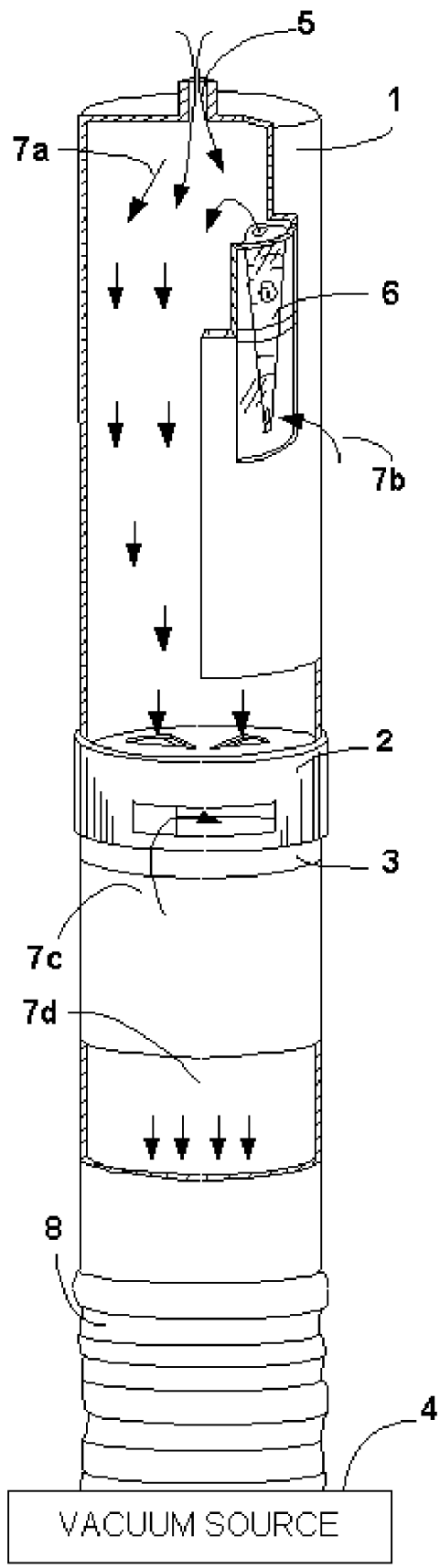
FIG. 1 is a cut-away perspective view of a vacuum attachment in accordance with the present fluid stream sampler showing the operation of the movable damper panel disposed in the flowpath.
Figure 6:
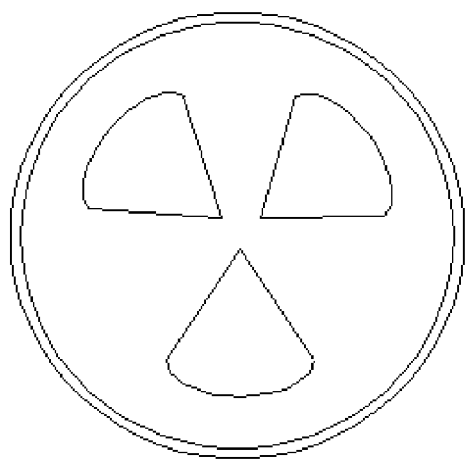
FIG. 6 is a plan view of the lower shell housing body.
Figure 7:
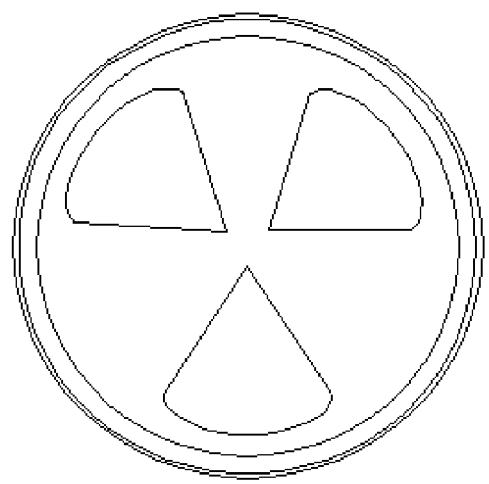
FIG. 7 is a plan view of the movable damper panel.
Figure 8:
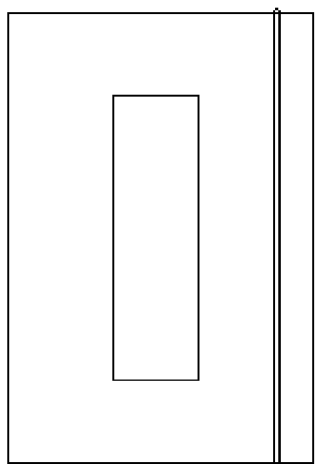
FIG. 8 is a elevation view of the lower shell housing body.
Figure 9:
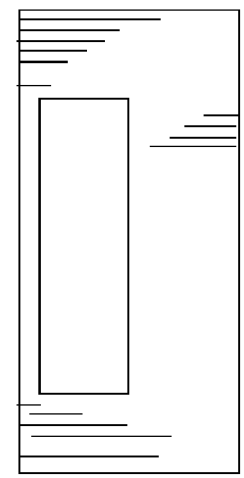
FIG. 9 is a elevation view of the movable damper panel.

Turning first to FIG. 1, reference numeral 1 depicts a preferred embodiment of the present fluid sampler that includes an upper shell housing body, preferably formed in a single piece from molded thermoplastic. The thermoplastic housing body can be formed by suitable molding techniques, such as, for example, blow, vacuum forming and/or injection molding.

As shown in FIG. 1, the variable damper panel ring 2 is preferably formed of material and using thermoplastic molding techniques similar to those used for the upper housing body. Vacuum source 4 imparts a vacuum that directs a fluid stream through the housing body along the flowpath that extends between the vacuum outlet opening and the sampling port inlet.

As shown in FIG. 1, reference numeral 3 depicts the preferred embodiment of the combined lower shell housing body, stationary damper panel and vacuum outlet opening and is preferably formed of material and using thermoplastic molding techniques similar to those used for the upper housing body.

As further shown in FIG. 1, sampling port inlet 5 has a molded protrusion for attachment to sampling media port outlets. Integrally molded rotameter 6 is visible through a transparent window disposed in the housing body.

As further shown in FIG. 1, the flowpath, represented by arrows 7a depicts the direction of fluid flow through the present fluid sampler port inlet 5 and into the internal cavity of the upper shell housing body 1 when a vacuum source is actuated. Flowpath arrow 7b represents the concurrent fluid flow direction through the integral rotameter 6 when a vacuum source is actuated. Flowpath arrow 7c represents the concurrent fluid flow direction through the variable damper panel 2 when a vacuum source is actuated. Flowpath arrow 7d represents the concurrent fluid flow direction to the vacuum source 4 when a vacuum source is actuated. Vacuum hose 8 is attached to the lower housing body at the vacuum outlet opening. FIG. 2 shows rotameter fluid inlet 9 disposed within the transparent window and exterior to the upper housing body.

As shown in FIG. 2, rotameter can be a conventional balltype float of steel, glass or plastic construction, as depicted by reference numeral 10. Two reference range lines 11, which are drawn on the transparent window 12 for viewing the rotameter in the upper housing body, permit volumetric flow rate readings to be taken. Additional incremental lines can be drawn on the window for a measurable range of flow rates.

As further shown in FIG. 2, a inverse conical half-form flow tube 13 is molded integrally with the upper housing body. FIG. 2 also illustrates the location of the fluid outlet opening 14 located in the top of flow tube, which is interior to the upper housing body.

Figure 11:
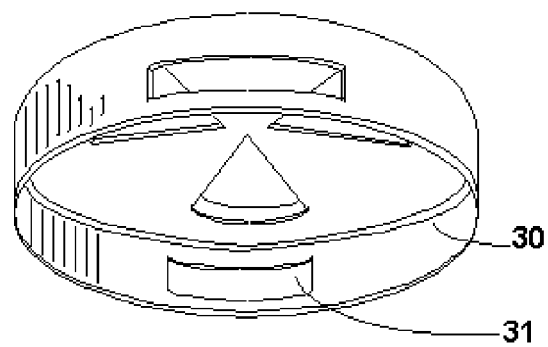
FIG. 11 is a perspective view of the underside of the movable damper panel.

FIG. 3 also illustrates a preferred embodiment of the molded annular protrusions 15 and 18 formed that stabilize and retain the movable damper panel ring close and adjacent to the exterior surface of the housing body upon imposition of vacuum flow within the housing body. The annular protrusions fit into the annular grooves 16 and 30 (see FIG. 11) when upper and lower housing bodies are assembled to damper panel ring during manufacturing. The friction fit of the annular assembly is such that the operator can make fine lateral adjustments of the damper panel ring with their fingers and the ring will remain in the desired position under the forces of the vacuum flow that surrounds it. FIG. 3 illustrates molded protrusion 19 formed in the damper panel ring as representing a knurled finish to enhance friction between an operator's fingers and the damper ring exterior surface when making lateral adjustment during operation.

Figure 10:
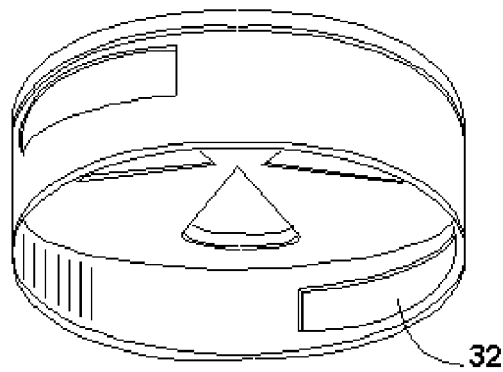
FIG. 10 is a perspective view of the underside of the lower shell housing body.

FIG. 3 also illustrates a preferred embodiment of the molded vent inlets 21 and 31 (see FIG. 11) as being located on opposite sides of the adjustable damper panel ring. FIG. 3 also illustrates a preferred embodiment of the molded vent inlets 22 and 32 (see FIG. 10) as being located on opposite sides of the stationary lower housing body and sized equally with vent inlet 21. When the upper and lower housing bodies are assembled to the damper panel ring, vent inlet 21 and 22 are located on adjacent planes, one interior to the other, and to be closely fitted when the damper panel ring inlet is moved laterally to a point forty-five degrees from the lower housing body inlet.

FIG. 3 additionally illustrates a preferred embodiment of the molded interior panel vents 17 and 20 as being located on the damper panel ring and the lower housing body respectively. The panel vents are shown as three pie-shaped holes. During manufacturing when the upper and lower housing bodies are assembled to the damper panel ring, the interior panel vents are located on adjacent planes, one atop the other and are closely fitted when the damper panel ring interior panel vents is moved laterally to a point forty-five degrees from the lower housing body interior panel vents. The overall effect of the interior panel vents and the vent inlets when in operation is to act as a vent for negative pressure developed within the housing body by the vacuum source via the hose that fluidly connects to the housing body to the vacuum source at the vacuum outlet opening. When the operator incrementally twists the damper panel ring from a lateral location between zero and forty-five degrees, the flowpath is diverted incrementally from a condition where the entire vacuum force is applied to the upper housing body with interior panel vent holes aligned open and vent inlets closed, to a condition where the entire vacuum force is applied to outside the housing body with interior panel vent holes closed and vent inlets aligned open. The effect being a wide range of flow rates for fluid sampling.

Turning now to FIG. 4, illustrating a preferred embodiment of the present fluid sampling vacuum chamber method that includes the present fluid sampler and the vacuum chamber 23 preferably formed from a conventional paper shipping tube. The paper shipping tube endcaps 24 and 25 are preferably of metal or plastic and are closely fitted to the ends of the shipping tube. Each endcap has a hole drilled into the face of the cap which closely fits the outside dimension of the fill port straw and the sample port inlet.

FIG. 4 also shows a preferred sampling media subassembly component constructed for the present vacuum chamber sampling method, that includes a flexible two-ply plastic heat sealed film gas bag 26 into which is constructed a interlayed and welded flexible two-ply plastic film self-sealing fill port valve 27 into which is inserted a rigid plastic fill port straw 28. The bag, valve and straw are to be each constructed to be impervious and inert to the fluids being sampled. In the preferred embodiment the gas bag and valve to be constructed using a heat impulse sealing machine with 2 mil thick polyvinyl fluoride film material. The straw to be constructed of virgin poly-tetrafluoroethylene material. The vacuum chamber gas bag subassembly is gas filled and purged with pure nitrogen and then vacuum-sanitary sealed in a outer plastic wrap prior to use.

In operation, an operator, who need not have substantial skill and experience in fluid stream sampling, can obtain an accurate volumetric quantity of fluid (usually air) that may be a parameter required for calculation(s) made to analyze a fluid stream sample collected on the medium. The sample is thus representative of the theoretical, statistically valid quantity of measured constituents, such as bioaerosol, aeroallergen particulate or gaseous chemicals in the fluid stream being analyzed. The fluid stream volumetric flow rate is preferably measured by a rotameter (see rotameter 6 in FIG. 1).

In the preferred method for obtaining a fluid stream sample in the media inside a vacuum chamber, a conventional household vacuum attachment hose can be connected to a conventional household vacuum cleaner, which serves as the vacuum source, at the end of the hose that is attachable to the vacuum outlet opening of the lower housing body.

The present fluid stream sampler should not normally be operated in an inverted position because, in the preferred embodiment, the rotameter element performs best when oriented upright, though some deviation from a upright should not substantially affect the performance outcome once calibrated.

The present fluid stream sampler should not normally be placed on sand, loose soil, or near loose surfaces because of the potential for physical interaction of the strong negative pressure within the housing body on these materials if disposed nearby on the sampler.

Prior to calibration and sampling, the vacuum chamber media can be prepared by removing the gas bag from the sanitary wrap. The operator should avoid touching the fill port straw end outside of the gas bag to any surface to ensure a cross-contamination free sample. The operator next inserts the fill straw partially through the endcap drilled hole (reference numeral 33 of FIG. 13), interior side first. The majority of the straw remains in the gas bag fill port valve. The operator inserts the gas bag assembly, bag first, into the empty vacuum chamber, in the preferred embodiment a paper shipping tube, and seals the ends with the form fitting endcap. The opposite endcap is confirmed to be in place on the end of the vacuum chamber shipping tube.

Upon actuation of the vacuum source for sampling, fluid stream volumetric flow rate calibration can be performed by adjusting the vacuum damper panel ring incrementally in a laterally twisting motion to vent or contain the internal negative pressure within the housing body, until the float ball of the rotameter (see reference numeral 10 in FIG. 2) rises to a level in the float tube that is within the reference range lines (see reference numbers 11 and 13 in FIG. 2). When so calibrated, the volumetric flow rate should then be at the flow rate specified by the manufacturer of the media being employed. In the case of the gas bag media at a flow rate consistent with standard procedures promulgated by environmental governmental regulatory agencies guidance and so as not to over inflate and rupture the gas bag prematurely. Typically the flow rate is translated to a gas bag aspiration rate of 3 liters per minute.

Once calibrated, the fluid sampler inlet can be inserted into the endcap hole opposite the inlet port straw endcap hole of the vacuum chamber. At this point the sample duration period begins. At the completion of the sample duration period, the present fluid sampler is removed from the vacuum chamber endcap hole and the fill port straw is removed from the endcap hole by gripping with the operator's fingers and pulling out briskly. The gas bag can be confirmed to be aspirated with a appropriate volume of sample fluid upon removal of the fill straw by removing either endcap and viewing (reference numeral 35 of FIG. 14). The gas bag will self-seal upon removal of the fill straw from the gas bag. The vacuum source can be deactuated. The vacuum chamber can now be prepared to be a shipping container by applying laboratory mailing labels and postage (reference numeral 34 of FIG. 13).

In the preferred method for obtaining a fluid stream sample on the media of a split impaction cassette or micro porous filter cassette, the fluid stream sampler calibrated as recommended for the vacuum chamber fill method. The flow rate necessary for cassette sampling media is typically greater than for gas bag media, and so would necessitate a different set of reference lines on the rotameter window if the present fluid sampler will be used for both media methods. Either type of cassette is prepared according to manufacturer's specifications, and can be attached to sampler port inlet opening (reference numeral 5 of FIG. 1). FIG. 5 shows a preferred sampling media, here represented by a split impaction sampling cassette 29 installed to the sampler port inlet opening located on top of the housing body.

The manufacturers of impaction cassettes and micro porous filter cassette media also generally recommend the sampling time intervals. Sampling intervals are typically between 0.5 and 15 minutes. At the completion of the sampling interval, the cassette is removed from the vacuum port inlet and sealed according to the cassette manufacturer's specifications. At this point in the method, the vacuum source can be deactuated. The cassette media can under the preferred embodiment, be enclosed with the sampled gas bag subcomponent inside the shipping container vacuum chamber with the endcaps attached. The shipping container with media inside can be mailed via ground postal carrier to a environmental laboratory for biochemical constituent analysis.

The foregoing methods can be repeated by moving the fluid stream sampler to a close by location with additional unused media installed, but in an environment known not to be contaminated with the subject constituents. The sample obtained during this form of repeated testing is referred to as a "background" sample. Background samples are typically taken upwind of the location of the known contamination source, or alternatively in a outdoor environment known to be substantially free of contaminants unless, the outdoor sample is the subject environment being analyzed. In that case, a background sample is taken in an indoor environment known to be substantially free of contaminants.

Based upon volume concentration calculations made to both subject and background samples, a correlation is made as to the degree of contamination compared to the background sample during biochemical analysis. Sampling methodology can now be considered complete, or alternatively the method can be repeated as necessary to obtain the desired confidence level for the survey.

The housing body, variable damper panel ring, rotameter flow tube and ball float should each be scaled in proportion to an average range of conventional household vacuum cleaner negative pressure outputs that are commonly available and should also be scaled in proportion to the regulated reduction in flow rate required by split impaction cassette and micro porous sampling cassette media. The vacuum chamber and gas bag subassembly subcomponent should be scaled to accommodate recommendations promulgated by governmental environmental regulatory agencies or environmental testing bodies. At a minimum the volume of the gas bag should be at least ten percent greater than the minimum volume required for biochemical analysis of the constituent being analyzed. The volume of the bag at a maximum limited by the sample interval duration recommendations for a subject environment and by the availability of conventional paper shipping tubes to accommodate needed volume.

While particular elements, embodiments and applications of the present invention have been shown and described, it will be understood, of course, that the invention is not limited thereto since modifications may be made by those skilled in the art, particularly in light of the foregoing teachings. It is therefore contemplated by the appended claims to cover such modifications as incorporate those features that come within the scope of the invention.

What is claimed is:

1. A fluid stream sampler for variable flow rate controlled air sampling, the sampler comprising:
   (a) a housing body having a vacuum outlet opening formed therein, a sampling port inlet formed therein, and a flowpath extending between the outlet opening and the inlet;
   (b) a volumetric flow rate indicator disposed in the flowpath between the vacuum outlet opening and the sampling port inlet;
   (c) a hose, fluidly connected at one end to a vacuum source, has a fitting at the other end thereof that is insertable into the vacuum outlet opening;
   (d) an adjustable damper panel interposed in the flowpath regulates the vacuum pressure within the housing body;
   whereby a vacuum imparted by the vacuum source directs a fluid stream through the housing body along the flowpath between the vacuum outlet opening and the sampling port inlet such that, upon moving the damper panel to a desired position within the flowpath, a desired volumetric flow rate is achieved as measured by the indicator, the desired volumetric flow rate corresponding to a preferred flow rate specified for a fluid constituent sampling medium interposed in the flowpath at the sampling port inlet.

2. The fluid stream sampler of claim 1 wherein the vacuum source is a household vacuum cleaner.

3. The fluid stream sampler of claim 1 wherein the volumetric flow rate indicator is a rotameter.

4. The fluid stream sampler of claim 1 wherein the fluid constituent sampling medium is either a split impaction cassette, a micro porous filter cassette or a gas bag.

5. The fluid stream sampler of claim 4 wherein the medium is capable of collecting at least one particulate for subsequent biological and chemical analysis.

6. The fluid stream sampler of claim 4 wherein the gas bag medium comprising:
   (a) a vacuum chamber having a inlet port formed therein and a outlet port formed therein;
   (b) a gas bag disposed in the vacuum chamber between the inlet port and the outlet port;
   (c) a valve disposed in the gas bag, having a inlet exterior to the bag and a outlet interior to the gas bag;
   (d) a straw disposed in the valve, having a inlet exterior to the vacuum chamber and a outlet interior to the gas bag;
   whereby a vacuum imparted by the fluid stream sampler at the outlet port directs a pressure drop interior to the vacuum chamber and a pressure differential effect on the atmosphere interior to the gas bag, such that, a fluid stream is developed at the straw inlet through the valve and into the interior of the gas bag.

7. The fluid stream sampler of claim 6 wherein the vacuum chamber is a paper shipping tube.

8. The fluid stream sampler of claim 6 wherein the valve is self-sealing.

9. The fluid stream sampler of claim 6 wherein the gas bag is capable of collecting gaseous air for subsequent biological and chemical analysis.

* * * * *